United States Patent
Hoogerhout et al.

(10) Patent No.: US 9,045,555 B2
(45) Date of Patent: Jun. 2, 2015

(54) VACCINE AGAINST AMYLOID FOLDING INTERMEDIATE

(75) Inventors: Peter Hoogerhout, Bilthoven (NL); Gerarda Petronella Johanna Maria Van Den Dobbelsteen, Bilthoven (NL)

(73) Assignee: DE STAAT DER NEDERLANDEN, VERT. DOOR DE MINISTER VAN VWS, Den Haag (NL)

(*) Notice: Subject to any disclaimer, the term of this patent is extended or adjusted under 35 U.S.C. 154(b) by 476 days.

(21) Appl. No.: 13/002,174

(22) PCT Filed: Jul. 1, 2009

(86) PCT No.: PCT/NL2009/050387
§ 371 (c)(1), (2), (4) Date: Mar. 28, 2011

(87) PCT Pub. No.: WO2010/002251
PCT Pub. Date: Jan. 7, 2010

(65) Prior Publication Data
US 2011/0182928 A1     Jul. 28, 2011

Related U.S. Application Data

(60) Provisional application No. 61/077,264, filed on Jul. 1, 2008.

(30) Foreign Application Priority Data

Jul. 1, 2008 (EP) ..................................... 08159385

(51) Int. Cl.
*A61K 39/385* (2006.01)
*C07K 7/64* (2006.01)
*A61K 38/12* (2006.01)
*A61P 25/28* (2006.01)
*C07K 14/47* (2006.01)
*A61K 38/17* (2006.01)

(52) U.S. Cl.
CPC ............. *C07K 14/4711* (2013.01); *A61K 38/12* (2013.01); *C07K 7/64* (2013.01); *A61K 39/385* (2013.01); *A61K 38/1716* (2013.01)

(58) Field of Classification Search
CPC ... A61K 38/1709; A61K 38/08; A61K 39/00; A61K 38/12; A61K 39/007; C07K 7/52
See application file for complete search history.

(56) References Cited

U.S. PATENT DOCUMENTS

2004/0043935 A1* 3/2004 Frangione et al. ............... 514/12
2011/0092445 A1* 4/2011 Barghorn et al. ............ 514/21.1

FOREIGN PATENT DOCUMENTS

| EP | 1676859 A1 * | 7/2006 |
| WO | WO 02055552 A2 | 7/2002 |
| WO | WO 2006121656 A2 | 11/2006 |

OTHER PUBLICATIONS

Lazo ND et al. (2005) On the nucleation of amyloid-beta protein monomer folding. Protein Sci. 14:1581-1596.*

(Continued)

*Primary Examiner* — Kimberly A Ballard
(74) *Attorney, Agent, or Firm* — Browdy and Neimark, PLLC

(57) ABSTRACT

The invention relates to an improved vaccine to treat Alzheimer's disease.

13 Claims, 5 Drawing Sheets

(56) References Cited

OTHER PUBLICATIONS

Melquiond A et al. (2008) Role of the region 23-28 in Abeta fibril formation: Insights from simulations of the monomers and dimers of Alzheimer's peptides Abeta 40 and Ab42. Curr. Alzheimer Res. 5:244-250.*

Baumketner A et al. (2008) Role of the familial Dutch mutation E22Q in the folding and aggregation of the 15-28 fragment of the Alzheimer amyloid-beta protein. PNAS, 105(16):6027-6032 (Edate: Sep. 25, 2007).*

Matsuzaki, et al., "Design synthesis, and biophysical properties of a helical ABeta1-42 analog: Inhibition of fibrillogenesis and cytotoxicity", Biochem. Biophys. Res. Comm, 2008, 371:777-780.

Sciarretta, et al., "ABeta40-Lactam(D23/K28) Models a Conformation Highly Favorable for Nucleation of Amyloid", Biochemistry, 2005, 44:6003-6014.

Cruz, et al., "Solvent and mutation effects on the nucleation of amyloid Beta-protein folding", Proc. Nat'l. Acad.Sci. USA, 2005, 102:18258-18263.

Oomen, et al., "Immunogenicity of Peptide-vaccine Candidates Predicted by Molecular Dynamics Simulations", J. Mol. Biol., 2003, 328:1083-1089.

Oomen, et al., "Crystal Structure of an Anti-meningococcal Subtype P1.4 PorA Antibody Provides Basis for Peptide-Vaccine Design", J. Mol. Biol., 2005, 351:1070-1080.

Bode, et al., "Validation of a solid-phase-bound steroid scaffold for the synthesis of novel cyclic peptidosteroids", J. Pept. Science, 2007, 13:702-708.

A. Olofsson et al., 2006, the solvent protection of Alzheimer amyloid-β(1-42) fibrils as determined by solution NMR spectroscopy, J. Biol. Chem. 281:477-83.

L. Yu et al., 2009, Structural characterization of a soluble amyloid β peptide oligomer. Biochemistry 48(9):1870-77.

S. Luna et al., 2013, Amyloid-β and APP Deficiencies Cause Severe Cerebrovascular Defects: Important Work for an Old Villain, PLoS One, Sep. 1, 2013 8(9):1-8, e75052. plus Supplemental Figure S1.

P. Hoogerhout et al., 2011, A Cyclic Undecamer Peptide Mimics a Turn in Folded Alzheimer Amyloid β and Elicits Antibodies against Oligomeric and Fibrillar Amyloid and Plaques, PLoS One, Apr. 2011, 6(4):1-6, e19110.

* cited by examiner

A

B

C

Aβ(25-30)  Aβ(24-29)  Aβ(23-28)
+ YNGK'    + YNGK'    + YNGK'

IgG-antibody titers of pooled sera against homologous peptide-BSA conjugates

VACCINE AGAINST AMYLOID FOLDING INTERMEDIATE

FIELD OF THE INVENTION

The invention relates to an improved vaccine which can be used to treat the Alzheimer's disease.

BACKGROUND OF THE INVENTION

It is estimated by the World Health Organization that 18 million people suffer from Alzheimer's disease worldwide (Vas et al. 2001). In the Netherlands, approximately 250,000 people have the Alzheimer's disease. The problem is expanding with increasing average age of the population. Care for a patient in a nursing home is estimated to cost € 30,000-60,000 per year (McDonnell et al. 2001). Vaccination would be cost-effective.

Alzheimer's disease is a conformational neurodegenerative disorder (Sadowski & Wisniewski 2004, Blennow et al. 2006, Editorials Nature Med. 2006). A characteristic of the disease is formation of plaques in the brain or in brain blood vessels. These plaques originate from a neuronal membrane-bound protein, the amyloid precursor protein. An α-helical fragment of 38-43 (typically 42) amino acid residues is cleaved enzymatically from the protein thus forming a peptide called "soluble Aβ β probably first adopts an extended conformation and is present in all body fluids. If soluble Aβ reaches a high concentration, it will undergo conformational changes and form aggregates. A plethora of aggregates has been found in vitro or in vivo, including multiple monomer conformers, different types of oligomers, Aβ-derived diffusable ligands, protofibrils, fibrils, and spheroids (adopted from Klein et al. 2004). Fibrillar Aβ has a cross-beta spine structure (Sawaya et al. 2007) and is eventually deposited in the brain to form the neurodegenerative plaques.

Immunization of transgenic mice (Schenk et al. 1999) and human patients in a phase I clinical trial (Hock et al. 2002) with a suspension of "pre-aggregated" Aβ 1-42 seemed to be beneficial. Antibodies in human immune sera recognized plaques, Aβ deposits and β-amyloid in brain blood vessels. The antibodies did not recognize the amyloid precursor protein or soluble Aβ.

A disadvantage of the "pre-aggregated" Aβ 1-42 suspension is that physical properties of this material are ill-defined. However, a far more serious problem was induction of meningoencephalitis as a vaccine-related side effect in 6% of the patients during a phase II clinical trial (Check 2002, Gilman et al. 2005). This side effect is caused by a cellular inflammatory reaction, attributed to a Th1 cellular response to epitopes located in the central and C-terminal part of Aβ 1-42 (McLaurin et al. 2002, Gelinas et al. 2004).

It has been demonstrated that beneficial antibodies induced by Aβ 1-42 are directed against the N-terminus (McLaurin et al. 2002, (Lee et al. 2005). It was therefore proposed to use C-terminally truncated Aβ peptides as immunogens (Sigurdsson et al. 2004, Lemere et al. 2006, Gevorkian et al. 2004, Lemere et al. 2007). Such short peptides are poorly immunogenic. In order to increase the immunogenicity, multiple copies of the peptide should be coupled to non-immunogenic carriers (with the aim of inducing IgM) or to carriers providing heterologous T cell epitopes (Agadjanyan et al. 2005, Ghochikyan et al. 2006, Maier et al. 2006, (Movsesyan et al. 2008)). In neither of these conjugates the peptide is expected to adopt the conformation of residues 4-10 as exposed by the β amyloid oligomers or pre-fibrils. Thus, antibodies induced with truncated peptide conjugates are expected to be weakly specific for the oligomers or pre-fibrils.

Therefore, there is still a need for an efficient medicament, preferably a vaccine against the Alzheimer's disease. The present invention provides an improved vaccine, which does not have all the drawbacks of existing vaccines: less to no toxicity and still able to induce an effective antibody response for immunization. The vaccine proposed in the present invention is a new analogue of the β-amyloid peptide.

DESCRIPTION OF THE INVENTION

Peptides of the Invention

In a first aspect of the invention, there is provided a peptide comprising the following sequence $X_1X_2X_3VGSN$-Z SEQ ID NO:1), $X_2X_3VGSNK$-Z (SEQ ID NO:2) or $X_3VGSNKG$-Z (SEQ ID NO:3), wherein $X_1$ is A or G, $X_2$ is E, G, Q or K, $X_3$ is D or N, and Z is an agent stabilizing the bend present within the peptide sequence $X_1X_2X_3VGSN$-Z (SEQ ID NO:1), $X_2X_3VGSNK$-Z (SEQ ID NO:2) or $X_3VGSNKG$-Z (SEQ ID NO:3). The peptides of the invention are modified peptides which shall be understood herein as peptides that are not a naturally occurring Aβ 1-42. Z may also be defined as an agent stabilizing the conformation of $X_1X_2X_3VGSN$ (SEQ ID NO:1), $X_2X_3VGSNK$ (SEQ ID NO:2) or $X_3VGSNKG$ (SEQ ID NO:3) as likely adopted in Aβ 1-42, preferably as adopted in Aβ 1-42. The peptide sequences $X_1X_2X_3VGSN$ (SEQ ID NO:1), $X_2X_3VGSNK$ (SEQ ID NO:2) and $X_3VGSNKG$ (SEQ ID NO:3) as identified above correspond respectively to amino acids 22-28 and 23-29 of Aβ 1-42. A preferred peptide sequence is $X_2X_3VGSNK$ (SEQ ID NO:2) which corresponds to amino acids 22-28 of Aβ 1-42. The different possible identities for $X_1$, $X_2$ and $X_3$ as indicated herein come from the presence of several known mutations within the human population in the sequence of Aβ 1-42: $X_2$ is amino acid 22 and is predominantly E in the population. However, the Arctic (E22G), Dutch (E22Q), and Italian (E22K) mutations are also known. Recently, another mutation has been identified (E22Δ) (Tomiyama et al. 2008). $X_3$ is amino acid 23 and is predominantly D. However, the Iowa mutation has already been identified (D23N). Therefore, it is obvious for the skilled person that if any other mutations would later be identified in a specific portion of Aβ 1-42 as identified herein; i.e. amino acid 21-27, 22-28 or 23-29, the sequence of the peptide of the invention may possibly be adapted to take into account of this later identified mutation.

Several overlapping peptide sequences were tested (see the example). As far as we are aware, two of the tested peptide sequences (aa 22-28 or 23-29) were found able to induce an antibody response in mice, which antibody was specifically able to recognize a conformational epitope of Aβ 1-42 as expressed in monomer, soluble oligomer (Haass and Selkoe 2007, Lambert et al, 2007, and Wash and Selkoe, 2007) fibrils, or neurodegenerative plaques. It seems that the recognition of oligomeric Ab is even more crucial than the recognition of fibril or plaque, since oligomeric Ab is more toxic to neurons. Clearance of soluble oligomers rapidly improves cognition while plaques are still present. The functionality of a peptide of the invention is preferably tested as set out in example 2: ELISA. The use of peptide-BSA conjugates as coating antigens in the ELISA allows determination of the anti-peptide titre, whereas coating of oligomeric and fibrillar Aβ 1-42 allows detection of specific cross-reactivity. The skilled person will understand that any other peptide sequence derived from Aβ 1-42 and incorporated in a peptide according to the invention and which is able to adopt the conformation of $X_1X_2X_3$VGSN, $X_2X_3$VGSNK or $X_3$VGSNKG as likely adopted in Aβ 1-42 is also encompassed by the present invention.

In an embodiment, the peptide of the invention consists of the formula $X_1X_2X_3$VGSN-Z, $X_2X_3$VGSNK-Z or $X_3$VGSNKG-Z, wherein $X_1$ is A or G, $X_2$ is E, G, Q or K, $X_3$ is D or N, and Z is an agent stabilizing the bend present within the peptide sequence $X_1X_2X_3$VGSN, $X_2X_3$VGSNK or $X_3$VGSNKG.

In a peptide of the invention, it is critical that the bend present within $X_1X_2X_3$VGSN, $X_2X_3$VGSNK or $X_1X_2X_3$VGSN is stabilised since we aim at designing a peptide which mimics a conformational epitope present in folded Aβ 1-42 as expressed in monomer, soluble oligomer, fibrils, or neurodegenerative plaques. Any way of achieving this stabilisation is encompassed by the present invention. The skilled person after having synthesized such a peptide of the invention may test its conformation by a method known in the art, for example by NMR as referred to in Example 1.

In one preferred embodiment, one first way of achieving this stabilisation is to cyclise a peptide of the invention. Therefore, a preferred peptide of the invention is a cyclic peptide. The skilled person knows how to cyclise a peptide. The actual cyclization reaction can be performed between any successive positions, including Z, in the sequence. In addition, the actual cyclization reaction can be performed on a precursor sequence not yet containing Z, but yielding Z as a result of the cyclization. Cyclisation can be carried out by linking, preferably by covalently linking, the N-terminal amino acid of the peptide sequence, preferably $X_1$, $X_2$ or $X_3$ in respectively $X_1X_2X_3$VGSN-Z, $X_2X_3$VGSNK-Z or $X_3$VGSNKG-Z, to Z. In this way, the C-terminal amino acid of the peptide sequences $X_1X_2X_3$VGSN, $X_2X_3$VGSNK or $X_3$VGSNKG is non-engaged in the cyclisation. Conveniently, cyclisation is performed in solid phase. For example, D23, side-chain linked to the solid phase, can be cyclised to E22, which on a carbonic acid linker yields cyclo-E22-D23. In another option D27, side-chain linked to the solid phase, can be cyclised to K28, which on amide linker yields cyclo-N27-K28. Preferably cyclisation is performed between amino acids in the contraloop Z, such as e.g. from D to G (becomes N-G) or from G to K*, if Z is YNGK. It is also possible to cyclise in solution, e.g. from G25 to S26 or from G to K*, if Z is YNGK. Cyclisation is thought to be important to stabilise the bend present within $X_1X_2X_3$VGSN, $X_2X_3$VGSNK or $X_3$VGSNKG.

Another preferred way of cyclisation of a peptide is to add a cysteine at the N- and C-termini of the peptide sequence, or by adding a cysteine at the N-terminus of the peptide sequence and another one to Z. The presence of two cysteines will allow to carry out a disulfide cyclisation, as is well-known to the skilled person.

In another preferred embodiment, a second way of achieving this stabilisation is to use Z. As earlier indicated herein, Z is an agent stabilizing the bend present within $X_1X_2X_3$VGSN, $X_2X_3$VGSNK or $X_3$VGSNKG in a peptide of the invention. In a preferred embodiment, Z stabilizes the bend present within $X_1X_2X_3$VGSN, $X_2X_3$VGSNK or $X_3$VGSNKG to ensure the peptide will likely adopt the conformation of folded Aβ 1-42. In a more preferred embodiment, Z stabilizes the bend present within $X_1X_2X_3$VGSN, $X_2X_3$VGSNK or $X_3$VGSNKG to ensure these peptides will adopt the conformation of folded Aβ 1-42. From studies, it is believed that there is a bend in conformation of folded Aβ 1-42, which bend is predicted to be present in a position corresponding to the position between the S and the N in $X_1X_2X_3$VGSN, $X_2X_3$VGSNK or $X_3$VGSNKG.

Z may be any agent known to the skilled person as stabilizing a bend, a turn or loop. Z may be defined as a "contra-turn" agent with a high probability to form a β-turn (Hutchinson et al., 1998; Woolfson et al., 1993). Z may be an amino acid, an oligopeptide, a peptide, a polypeptide, a protein, an antigen, a mono- or oligosaccharide, and/or a steroid. In a preferred embodiment, Z is a peptide fragment of 8, 7, 6, 5 or 4 amino acid, in increasing preference with decreasing length. Preferably the peptide fragment of 4-8 amino acids is a "contra-turn" agent with a high propensity for a β-turn conformation. A preferred peptide fragment is a tetrapeptide selected from the group consisting of YNGK (SEQ ID NO:5), TCGV (SEQ ID NO:6), CGNT (SEQ ID NO:7), LCGT (SEQ ID NO:8), LKGT (SEQ ID NO:9), GAIK (SEQ ID NO:10), GAIC (SEQ ID NO:11), AIIK (SEQ ID NO:12), and AIIC (SEQ ID NO:13). More preferably, the tetrapeptide is selected from the group consisting of YNGK (SEQ ID NO:5), TCGV (SEQ ID NO:6), CGNT (SEQ ID NO:7), LCGT (SEQ ID NO:8) and LKGT (SEQ ID NO:9). Most preferably, the tetrapeptide is selected from the group consisting of YNGK (SEQ ID NO:5), TcGV (SEQ ID NO:14), CGNT (SEQ ID NO:7), LcGT (SEQ ID NO:16) and LkGT (SEQ ID NO:17), wherein c=D-Cys and wherein k=D-Lys (see e.g., Oomen et al. 2003; and Oomen et al. 2005). Examples of proteins that may be used for Z are HSA, IgG's and other serum proteins. Examples of antigens are (bacterial) toxins and virus-like particles. Z may also be a steroid scaffold such as described in e.g., Bode et al. (2007, *J. Pept. Sci.*, 13:702-708) Suitable steroid scaffold for use as Z include e.g. bile acids and derivatives thereof such as e.g. cholic acid, deoxycholic acid and methyl 7-α-acetoxy-3α-amino-12α-amino-5β-cholan-24-oate. Preferably in the peptides of the invention, the peptide sequences are connected to the C-3 and C-12 positions of the steroid scaffold, e.g., as described by Bode et al. (2007, supra).

Z may be linked to the peptide sequence before cyclisation and optionally cyclised together with the rest of the peptide sequence. In this embodiment, Z is preferably a relatively short molecule like an oligopeptide: an amino acid, a dipeptide, a tripeptide, a tetrapeptide, a pentapeptide. In this preferred embodiment, the total number of amino acids (from the peptide sequence originating from Aβ 1-42 and from Z) is preferably ten or eleven. Even more preferably, this number is eleven. Z may comprise or consist of an amino acid present in the corresponding Aβ 1-42 sequence to align with the corresponding $X_1X_2X_3$VGSN, $X_2X_3$VGSNK or $X_3$VGSNKG sequence.

Alternatively, Z may be linked to the cyclised peptide sequence. In this embodiment, Z may be a relatively bigger molecule than in the previous embodiment: a polypeptide or a protein for example.

Best results were obtained when both ways are combined (cyclisation and the presence of Z) for stabilizing the peptide. Even more preferably, Z is linked to the peptide sequence and is subsequently cyclised with the rest of the peptide sequence. Alternatively, Z is formed as a result of the cyclization reaction. Within this preferred embodiment, best results were obtained with Z being the tetrapeptide as defined above, such as e.g. YNGK. More preferably, the tetrapeptide comprises at least one of a cysteine and a lysine to allow selective conjugation of the peptide to a carrier molecule as described below. The lysine preferably is a modified lysine such as $N^\epsilon$-(S-acetylmercaptoacetyl)lysine (Lys-SAMA). The presence of at least one of a cysteine and a Lys-SAMA residue in the tetrapeptide allows for selective conjugation of the peptide of the invention to a sulfhydryl-reactive carrier such as a carrier protein.

In a most preferred embodiment, there is provided a peptide consisting of the formula $X_2X_3$VGSNK-Z wherein $X_2$ is E, G, Q or K, $X_3$ is D or N and Z is an agent stabilizing the bend present within $X_2X_3$VGSNK. Preferably, Z is YNGK, wherein even more preferably, K in YNGK is a modified lysine (Lys-SAMA) to allow selective conjugation of the peptide.

In another most preferred embodiment, there is provided a peptide comprising the following sequence $X_3$VGSNKG-Z, wherein $X_3$ is D or N and Z is an agent stabilizing the bend present within $X_3$VGSNKG. Preferably, Z is YNGK wherein even more preferably, K in YNGK is a modified lysine (Lys-SAMA) to allow selective conjugation of the peptide.

A peptide comprising the sequence $X_2X_3$VGSNKGAI-Z wherein $X_2$ is E, $X_3$ is D, and Z is a modified lysine (Lys-SAMA) and a peptide comprising the sequence VGSNKG-Z wherein Z is a modified lysine (Lys-SAMA) were both found to generate antibody responses to the immunizing peptides themselves, however the thus generated antibodies failed to cross react with oligomer or fibrillar A$\beta$ 1-42.

A peptide of the invention may be present as a single peptide or incorporated into a fusion molecule, such as a fusion protein. A peptide may further be modified by deletion or substitution of one or more amino acids, by extension at the N- and/or C-terminus with additional amino acids or functional groups, which may improve bio-availability, targeting to T-cells, or comprise or release immune modulating substances that provide adjuvant or (co)stimulatory functions. The impact of these modifications is preferably tested on the conformation of the synthetised peptide. This may be done by NMR for example. It is important that in a thus obtained peptide, the conformation of $X_1X_2X_3$VGSN, $X_2X_3$VGSNK or $X_3$VGSNKG as likely adopted in A$\beta$ 1-42, preferably as adopted in A$\beta$ 1-42 has not been modified. The optional additional amino acids at the N- and/or C-terminus are preferably not present in the corresponding positions in the amino acid sequence of the protein it derives from, i.e. the A$\beta$ 1-42 amino acid sequence. Therefore, in an even more preferred embodiment, in order to improve the immunogenicity of a peptide of the invention, this peptide, preferably a cyclic peptide as described above is conjugated to an immunogenic carrier molecule, preferably selectively through linkage of Z and the immunogenic carrier molecule. Such a peptide is called a conjugated peptide. Therefore, in a preferred embodiment, a peptide of the invention is a conjugated peptide, more preferably a conjugated cyclic peptide. An immunogenic carrier molecule preferably is a carrier that when conjugated to a peptide of the invention induces an immune response to the peptide of the invention upon administration to a subject such as a mammal. The immunogenic carrier may also have adjuvant-activity as later defined herein. Numerous of immunogenic carrier molecules are known to the skilled person (Hermanson, G. T., 1996, *Bioconjugate techniques*. Academic Press, San Diego; Drijfhout and Hoogerhout, 2000). Suitable immunogenic carrier molecules include e.g. bacterial toxins or toxoids such as exotoxins and variants thereof with reduced toxicity. Preferred immunogenic carrier molecules include diphtheria toxoid $CRM_{197}$, a serum albumin (e.g. human serum albumin) and tetanus toxoid (Beuvery et al., 1986; Claesson et al., 2005).

Composition

In a further aspect, there is provided a composition comprising a peptide as defined herein. Such a composition may be a pharmaceutical composition or a medicament.

In a further preferred embodiment, a peptide or a peptide composition further comprises a pharmaceutical excipient and/or a pharmaceutically acceptable carrier and/or an immune modulator. Any known inert pharmaceutically acceptable carrier and/or excipient may be added to a composition. Formulation of medicaments, and the use of pharmaceutically acceptable excipients are known and customary in the art and for instance described in Remington; The Science and Practice of Pharmacy, $21^{nd}$ Edition 2005, University of Sciences in Philadelphia.

A pharmaceutical composition may further comprise pharmaceutically acceptable stabilizing agents, osmotic agents, buffering agents, dispersing agents, and the like. The preferred form of the pharmaceutical composition depends on the intended mode of administration and therapeutic application. The pharmaceutical carrier can be any compatible, non-toxic substance suitable to deliver the active ingredients, i.e. a peptide to a patient. Pharmaceutically acceptable carriers for intranasal delivery are exemplified by water, buffered saline solutions, glycerin, polysorbate 20, cremophor EL, and an aqueous mixture of caprylic/capric glyceride, and may be buffered to provide a neutral pH environment. Pharmaceutically acceptable carriers for parenteral delivery are exemplified by sterile buffered 0.9% NaCl or 5% glucose optionally supplemented with a 20% albumin. Preparations for parental administration must be sterile. The parental route for administration of the active ingredients is in accord with known methods, e.g. injection or infusion by subcutaneous, intravenous, intraperitoneal, intramuscular, intraarterial or intralesional routes. A composition of the invention is preferably administered by bolus injection. A typical pharmaceutical composition for intramuscular injection would be made up to contain, for example, 1-10 ml of phosphate buffered saline and 1 to 100 µg, preferably 15-45 µg of a modified conjugated peptide. For oral administration, the active ingredient can be administered in liquid dosage forms, such as elixirs, syrups, and suspensions. Liquid dosage forms for oral administration can contain colouring and flavouring to increase patient acceptance.

Methods for preparing parenterally, orally or intranasally administrable compositions are well known in the art and described in more detail in various sources, including, for example, Remington's Pharmaceutical Science (15th ed., Mack Publishing, Easton, Pa., 1980) (incorporated by reference in its entirety for all purposes).

Any known immune modulator, in particular modulators leading to a balanced Th2/Th1 response, like aluminium phosphate or aluminium hydroxide, may be added to a composition. Preferably, the immune modulator is an adjuvant. More preferably, the composition comprises a peptide as earlier defined herein and at least one adjuvant. An adjuvant is herein defined to include any substance or compound that, when used in combination with a peptide, to immunise a mammal, preferably a human, stimulates the immune system, thereby provoking, enhancing or facilitating the immune response against the peptide, preferably without generating a specific immune response to the adjuvant itself. Preferred adjuvants enhance the immune response against a given antigen by at least a factor of 1.5, 2, 2.5, 5, 10 or 20, as compared to the immune response generated against the peptide under the same conditions but in the absence of the adjuvant. Tests for determining the statistical average enhancement of the immune response against a given peptide as produced by an adjuvant in a group of animals or humans over a corresponding control group are available in the art. An adjuvant as used herein will usually be a compound that is foreign to a mammal, thereby excluding immunostimulatory compounds that are endogenous to mammals, such as e.g. interleukins, interferons and other hormones.

A composition of the present invention may contain at least one adjuvant. An adjuvant used in the present invention will be selected so that the effect of the peptide is not inhibited. Adjuvants used in the present invention are those which are physiologically acceptable to humans, these include, but are not limited to aluminium hydroxide, aluminium phosphate, oil/surfactant based emulsion adjuvants such as Montanide™ in which different surfactants (especially mannityl oleate) are combined with a mineral oil, squalene-containing emulsions such as MF59™, monophosphoryl lipid A, or Neisseriae mutant lipopolysaccharide (as described in PCT/NL98/ 0063).

A medicament may be administered as a single administration. Alternatively, the administration of a peptide as earlier herein defined and/or an adjuvant may be repeated if needed and/or distinct peptides and/or distinct adjuvants may be sequentially administered. Peptide, composition and medicament of the invention are preferably formulated to be suitable for intravenous or subcutaneous, or intramuscular administration, although other administration routes can be envisaged, such as mucosal administration or intradermal and/or intracutaneous administration, e.g. by injection.

Accordingly in a preferred embodiment, a peptide as described herein is for use as a medicament. More preferably, this medicament is a vaccine against the Alzheimer's disease. Even more preferably, the medicament is for preventing, delaying and/or treating the Alzheimer's disease. A vaccine as defined herein may be used for the prophylactic protection against the Alzheimer's disease or for the treatment of this disease.

In the context of the invention, an organism or an individual or a subject may be an animal or a human being. Preferably, the organism is a human being. Preferably, an organism treated is suspected to have a high risk of developing the Alzheimer's disease due for example to potential genetic predisposition, and/or to the age of the subject and/or to the lifestyle of a subject (for example nutritional habit and/or to the absence of physical activity) and/or to any other known parameter indicating this subject has an increased risk of developing the Alzheimer's disease.

The term "prevention" shall be understood to include complete prevention, prophylaxis, as well as lowering the individual's risk of falling ill with said disease or condition and delaying the onset of the disease or condition. The term "prevention" thus also comprises the treatment of persons suspected to be at risk falling ill with said disease or condition. The term shall also be understood to include alleviation of symptoms already developed.

The term "delaying" used herein means administration of a peptide to an organism, i.e. a patient being in a pre-stage of the condition to be treated in which patients a pre-form of the corresponding condition is diagnosed by methods known in the art.

The term "treatment" or "treating" "is understood the management and care of a patient for the purpose of combating the disease, condition, or disorder.

Within the context of the invention, "treating the Alzheimer's disease and/or delaying its progression" preferably means that a therapeutically effective amount of a peptide is added. It refers to an amount effective, at dosages and for periods of time necessary, to achieve the desired therapeutic result, i.e. treat the Alzheimer's disease and/or delay its progression.

The amount of a peptide may vary according to factors such as the disease state, age, sex, and weight of the individual, and the ability of the pharmacological agent to elicit a desired response in the individual.

A therapeutic effect (leading to treating the Alzheimer's disease and/or delaying its progression) is preferably one that results in at least one of:
  a reduction of the load of beta plaques present in the brain;
  a reduction of the amount of soluble $A\beta$ oligomers or prefibrils present in the brain; and,
  a reduction of the severity of a symptom associated with the Alzheimer's disease.

A reduction in the load of beta plaques present in the brain of a treated patient preferably means that the amount of a peptide added will be able to prevent de novo formation of beta plaques to at least some extent and/or that existing plaques will be to at least some extent inhibited in their ability to expand. Preferably, in this context, the deposition of beta plaques will not increase in a treated patient in terms of beta plaque load as identified by using an imaging technique such as PET scan (Henriksen, Yousefi et al., 2008) and/or magnetic resonance imaging (MRI) (O'Brien, 2007). In a PET scan, the quantity of beta plaque load is proportional to the tracer uptake. Preferably, the load of beta plaques will decrease of at least 2%, 5%, 10%, 20%, 25%, 30%, 35%, 40%, 45%, 50%, 55%, 60%, 65%, 70%, 75%, 80%, 85%, 90%, 95% or more. Even more preferably, no beta plaque will be detected. The skilled person knows that the visualisation of beta plaque should be done approximately at least one day, at least one week, at least one month after vaccination or more. (Meyer-Luehmann, Spires-Jones et al., 2008). If need be, one may decide to vaccinate several times and to regularly monitor the load of beta plaques.

A reduction of the amount of soluble $A\beta$ oligomers or prefibrils present in the brain of a treated patient preferably means that the amount of a peptide added will be able to prevent de novo formation of soluble $A\beta$ oligomers or prefibrils to at least some extent and/or that existing soluble $A\beta$ oligomers or prefibrils will be to at least some extent inhibited in their ability to expand. Preferably, in this context, the amount of soluble $A\beta$ oligomers or prefibrils will not increase in a treated patient in terms of a surface as identified by an imaging technique as defined above. Preferably, the amount of soluble $A\beta$ oligomers or prefibrils will decrease of at least 2%, 5%, 10%, 20%, 25%, 30%, 35%, 40%, 45%, 50%, 55%, 60%, 65%, 70%, 75%, 80%, 85%, 90%, 95% or more. More preferably, the amount of soluble $A\beta$ oligomers or prefibrils will not be detectable using the same method.

In the context of the invention, a soluble $A\beta$ oligomer, prefibril or protofibril is an indication for an assembly of 2-24 $A\beta$ monomers (Haas and Selkoe 2007).

Within the context of the invention, "a reduction of the severity of a symptom associated with Alzheimer's disease" preferably means an improvement of cognition as measured with a psychological test to assess the improvement of cognition in patients suffering from the Alzheimer's disease.

Use

Accordingly, in a further aspect, there is provided the use of a peptide or of a composition as defined herein for the manufacture of a medicament against the Alzheimer's disease. Preferably, the medicament is a vaccine. More preferably, the vaccine is for preventing, delaying and/or treating the Alzheimer's disease.

Accordingly, in another further aspect, there is provided a method of preventing, delaying and/or treating the Alzheimer's disease by administering a peptide or a composition as defined herein to a patient in a need thereof.

Method of Synthesising a Peptide

The art currently knows many ways of generating a peptide of the invention. The invention is not limited to any ways of generating a peptide as long as the generated peptide comprises, consists or overlaps with any of the given modified sequences as identified herein and had the required conformation as earlier defined herein.

Accordingly, in a further aspect there is provided a method for producing a modified cyclic peptide as defined herein, said method comprising the following steps: synthesizing synthesising a cyclic peptide comprising the sequence $X_1X_2X_3$VGSN-Z (SEQ ID NO:1), $X_2X_3$VGSNK-Z (SEQ ID NO:2) or $X_3$VGSNKG-Z (SEQ ID NO:3), wherein $X_1$ is A or G, $X_2$ is E, G, Q or K, $X_3$ is D or N, and Z is an agent stabilizing the bend present within the peptide sequence $X_1X_2X_3$VGSN (SEQ ID NO:1), $X_2X_3$VGSNK (SEQ ID NO:2) or $X_3$VGSNKG (SEQ ID NO:3); and optionally conjugating an immunogenic carrier molecule to the cyclic peptide obtained in b), preferably through linkage of Z to the immunogenic carrier molecule.

Each step of this method is known to the skilled person and has been extensively described in the example.

Antibody

In a further aspect, there is provided an antibody directed against a modified (cyclic) peptide of the invention as defined herein. The skilled person knows how to produce such an antibody in an animal. Methods for generating antibodies or antibody-fragments that specifically bind to a given polypeptide are described in e.g. Harlow and Lane (1988, Antibodies: A Laboratory Manual, Cold Spring Harbor Laboratory Press, Cold Spring Harbor, N.Y.) and WO 91/19818; WO 91/18989; WO 92/01047; WO 92/06204; WO 92/18619; and U.S. Pat. No. 6,420,113 and references cited therein. The term "specific binding," as used herein, includes both low and high affinity specific binding. Specific binding can be exhibited, e.g., by a low affinity antibody or antibody-fragment having a Kd of at least about $10^{-4}$ M. Specific binding also can be exhibited by a high affinity antibody or antibody-fragment, for example, an antibody or antibody-fragment having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater.

Diagnostic Methods

In a further aspect, there is provided a method for diagnosing a neurodegenerative disease or condition, such as Alzheimer's disease. The method comprises determining the presence or absence of a beta amyloid plaque (i.e. neurodegenerative plaque) in the brain of a patient using an antibody as defined herein. Preferably in the method, the presence of a beta amyloid plaque in the subject's brain (or a sample thereof) is indicative for the subject being at risk of developing a neurodegenerative disease or condition such as Alzheimer's disease or indicative for the diagnosis of the neurodegenerative disease or condition, such as Alzheimer's disease. Preferably, such method is used for prognosing or diagnosing Alzheimer's disease in the brain of a patient. In the context of the invention, diagnosis means either a predictive risk assessment of a subject for developing later the Alzheimer's disease or preferably an assessment of the development of the Alzheimer's disease in a subject. In the context of the invention, a subject may be an animal or a human being. Preferably, a subject is a human being.

According to a preferred embodiment, the method is carried out in vitro or ex vivo in a sample obtained from a subject. The sample preferably comprises brain tissue isolated from a subject. More preferably, the tissue is brain blood vessel.

Preferably, a detection of the presence of a beta amyloid plaque is revealed by the binding of an antibody of the invention to a brain sample as assayed by ELISA as explained in the example. The diagnosis method may be sequentially applied to a subject to monitor the development of the disease.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a peptide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way

EXAMPLES

Example 1

Synthesis Strategy

We tested truncated peptides of Aβ, which do not comprise the immunodominant N-terminal B cell epitope. We aim at targeting an antibody response to early misfolded Aβ.

The sequence of Aβ1-42 is:

```
                                              (SEQ ID NO: 4)
DAEFR⁵HDSGY¹⁰EVHHQ¹⁵KLVFF²⁰AEDVG²⁵SNKGA³⁰IIGLM³⁵

VGGVV⁴⁰IA.
```

The structure of Aβ1-42 fibrils has been resolved by NMR spectroscopy (Olofsson et al. 2006). Hydrogen/deuterium exchange experiments with fibrils showed that the regions $Glu^{11}$-$Gly^{25}$ and $Lys^{28}$-$Ala^{42}$ in the Aβ sequence are shielded from solvent, whereas the N-terminus $Asp^1$-$Tyr^{10}$ and the two-residue fragment $Ser^{26}$-$Asn^{27}$ are solvent-accessible.

Figure 1:
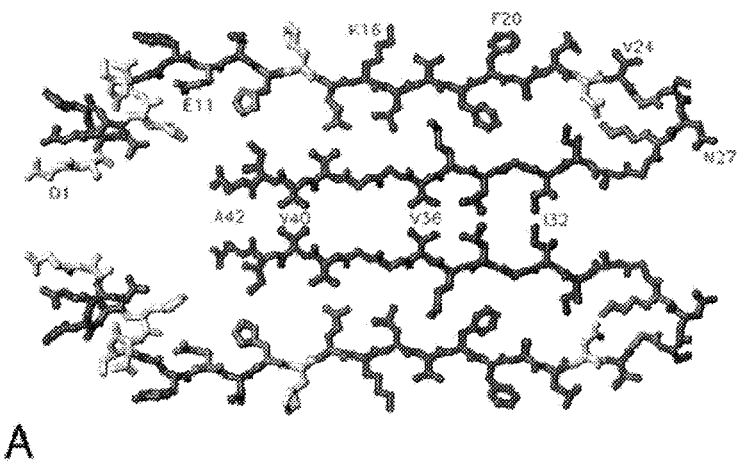
FIG. 1. Model of an Aβ 1-42 fibril. A and B represent a dimeric cross-β unit and C the assembled fibril. [Credit: Olofsson et al. 2006 J. Biol. Chem. 281, 477-483].
Figure 1:
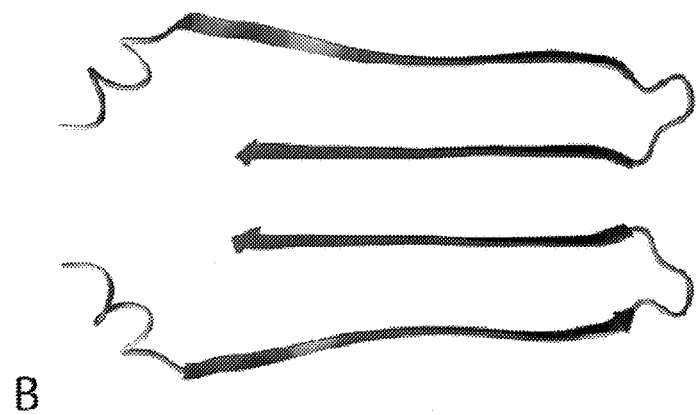
Figure 1:
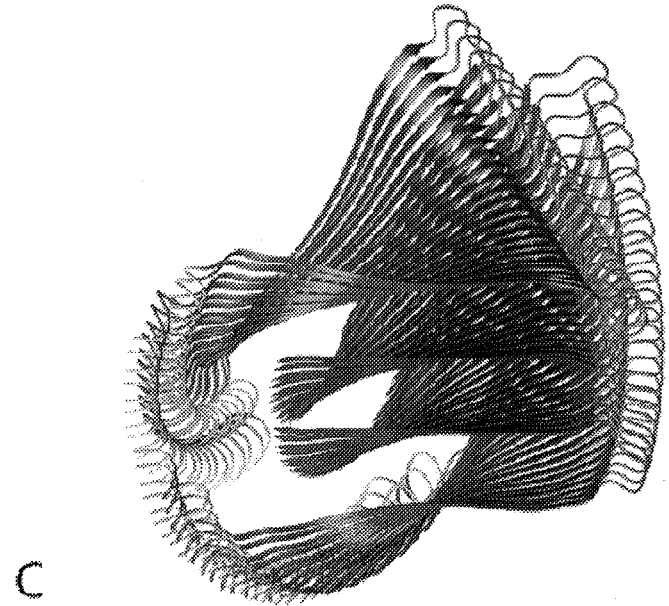

The NMR data are consistent: Asp$^1$-Tyr$^{10}$ and the two-residue fragment Ser$^{26}$-Asn$^{27}$ are solvent-accessible. The NMR data are consistent with a model of the fibril as depicted in FIG. 1C. The predicted structure is a twisted cross-β spine. FIGS. 1A and 1B show a section, the dimeric cross-β unit. Within the dimer, each monomer contains two antiparallel β sheets which are connected by a turn composed of Ser$^{26}$-Asn$^{27}$.

Figure 2:
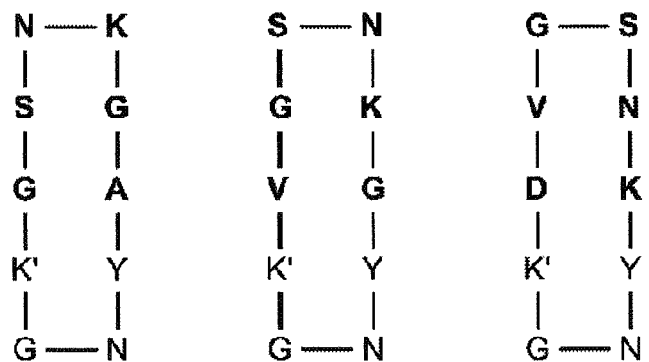
FIG. 2. Sequences of amyloid-derived cyclic peptides (K* is a modified lysine residue for conjugation purposes).
Figure 3:
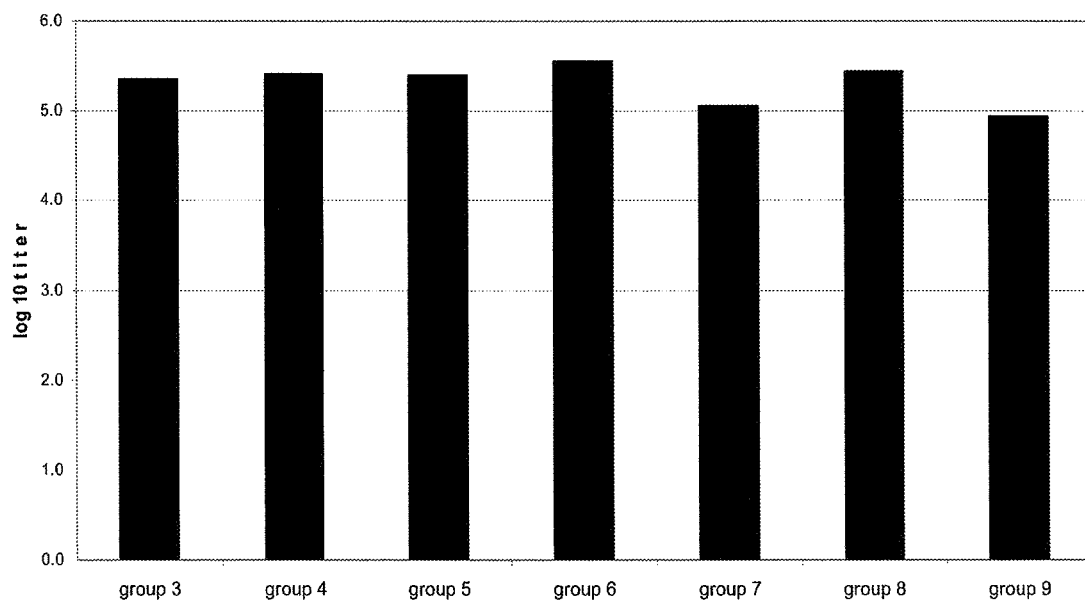
FIG. 3: IgG-antibody titres of pooled mice sera against homologous peptide-BSA conjugates. The titre is the $^{10}$log of the reciprocal serum dilution at 50% of the maximum optical density at 450 nm in ELISA.

Based on the amyloid fibril model (FIG. 1), we decided to prepare a set of YNGK*-stabilized cyclic 10 and 11 mer amyloid peptides. FIG. 2 shows the aimed amyloid decapeptides. We hypothesized that we could stabilise the conformation of small Aβ peptides by adding an artificial sequence YNGK*, in which K* is a modified lysine residue for selective conjugation to a carrier protein, followed by main chain ("head to tail") amide cyclization (Oomen et al (2005)). Likewise, we prepared a small panel of cyclic decameric and undecameric peptides spanning six or seven residues from the region 21-31 of Aβ and YNGK* (see Table 1).

TABLE 1 synthetised peptides

| Group | Antigen | Peptide code | peptide MH$^+$ found/calculated |
|---|---|---|---|
| 1 | oligomeer Aβ 1-42 | — | — |
| 2 | fibrillair Aβ 1-42 | — | — |
| 3 | lineair Aβ(22-28)/TTd | S070-07 | 1367.8/1367.6 |
| 4 | cyclo-Aβ(25-30)/TTd | S060-08 | 1093.5/1093.5 |
| 5 | cyclo-Aβ(24-29)/TTd | S060-09 | 1121.5/1121.5 |
| 6 | cyclo-Aβ(23-28)/TTd | S060-10 | 1179.6/1179.5 |
| 7 | cyclo-Aβ(24-30)/TTd | S061-56 | 1192.7/1192.5 |
| 8 | cyclo-Aβ(23-29)/TTd | S060-05 | 1236.5/1236.5 |
| 9 | cyclo-Aβ(22-28)/TTd | S060-06 | 1308.7/1308.6 |
| 10 | cyclo-Aβ(21-27)/TTd | S076-08 | 1251.5/1251.5 |

Example 2

Specificity of Some of the Modified Cyclised Peptides for a Conformational Epitope of Folded Aβ 1-42

Figure 4A:
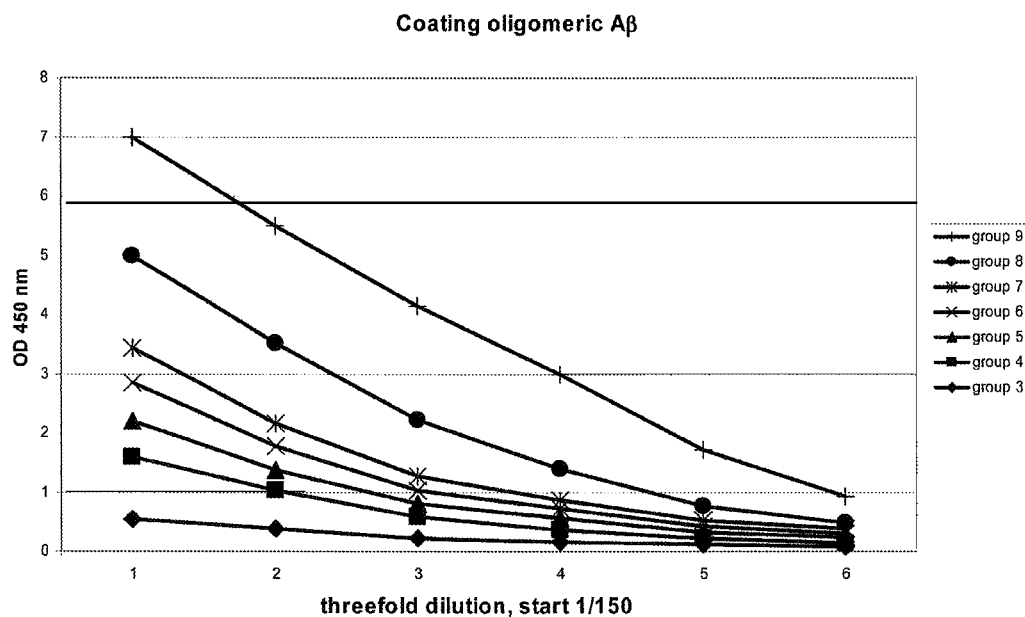
FIG. 4: OD450 nm of pooled mice sera as a function of dilution with coating oligomeric or fibrillar Aβ 1-42.
Figure 4B:
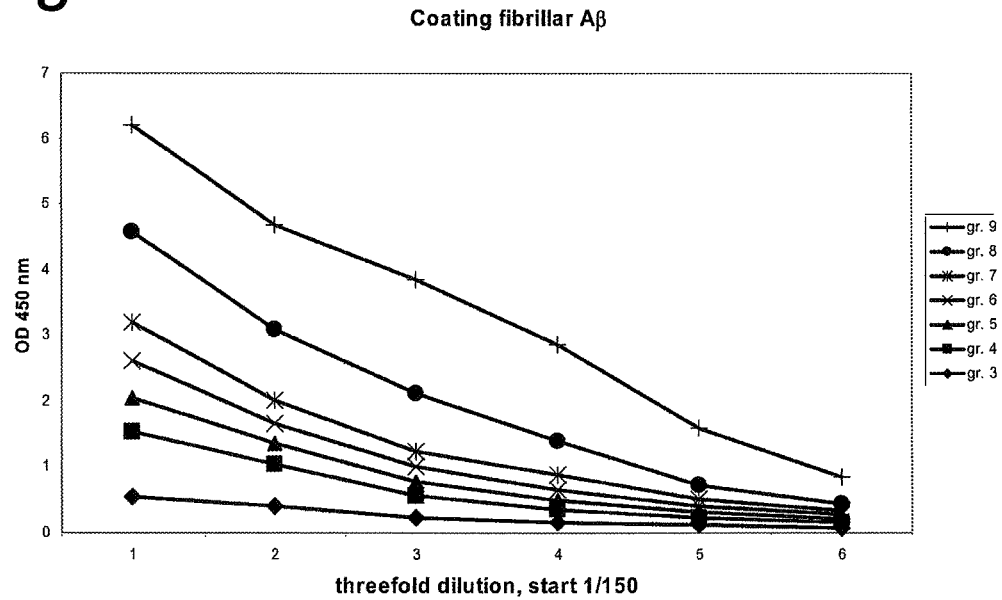
Figure 5A:
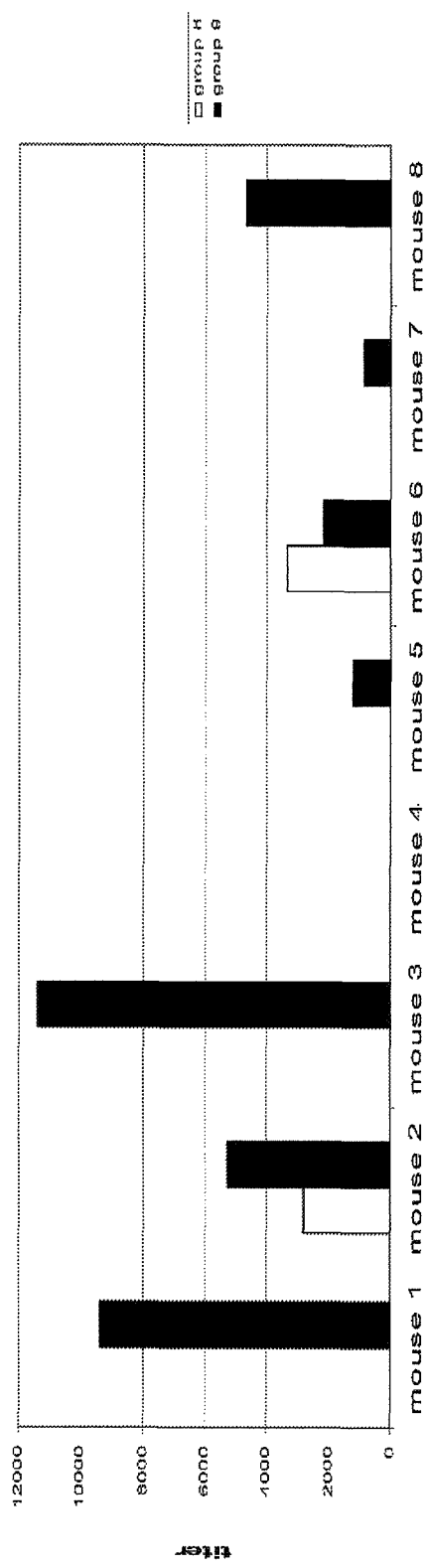
FIG. 5: IgG antibody titers of individual mice sera of groups 8 and 9 against oligomeric or fibrillar Aβ 1-42 The titre is the reciprocal serum dilution at 50% of the maximum optical density at 450 nm in ELISA.
Figure 5B:
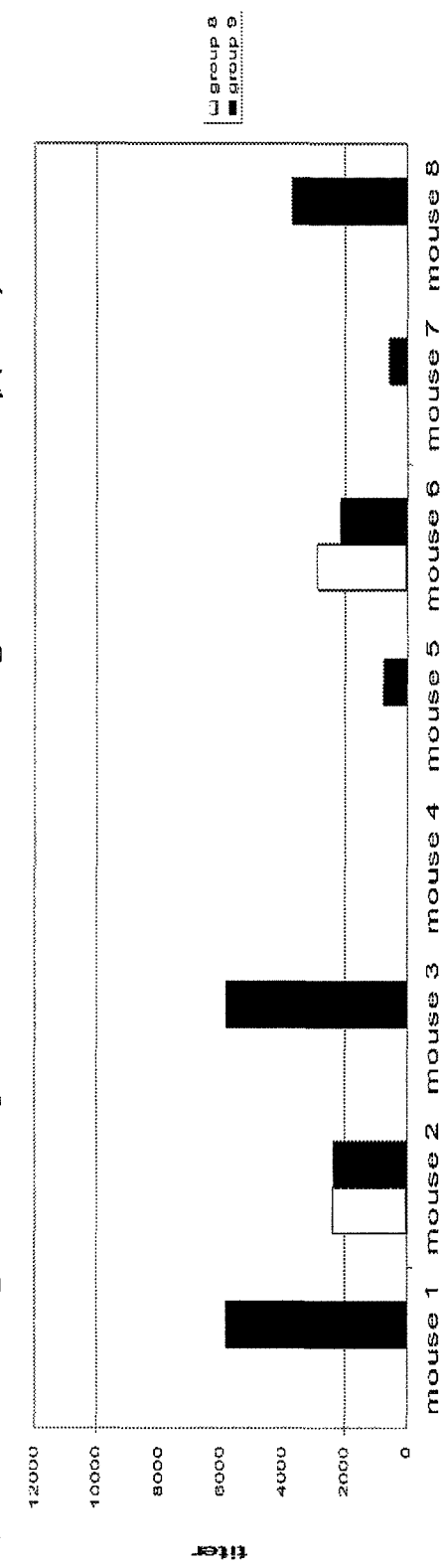
Figure 6A:
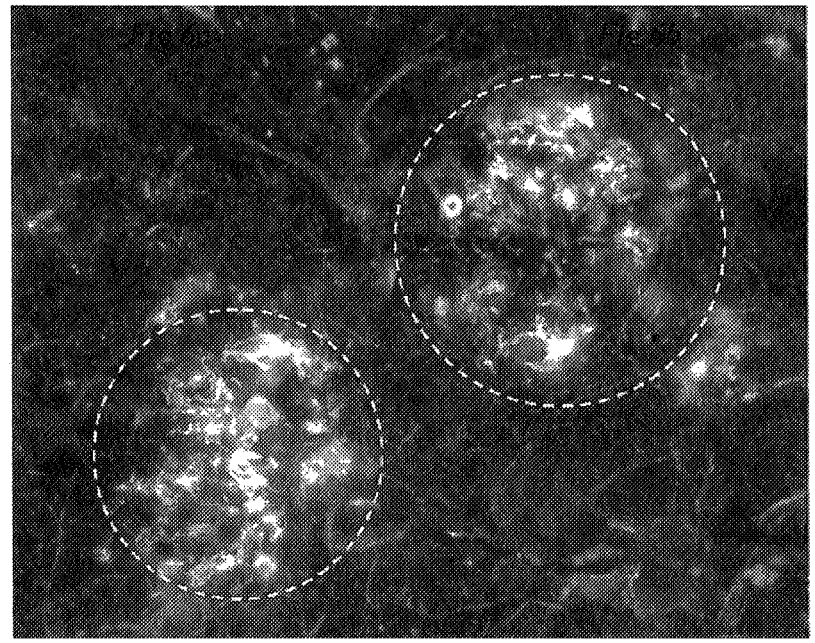
FIG. 6: Immunohistochemical staining of human brain section donor 99-30 (Braak 6) with a mouse serum (1:300) immunized with cyclo[Aβ(22-28)-YNGK]/tetanus toxoid conjugate (a) and the control monoclonal 6E10 (1:15.000) in (b). Similar pattern of plaques were recognized by the mouse sera as positive control. (Microscope: Leica DMRE fitted with a DC300 camera)
Figure 6B:
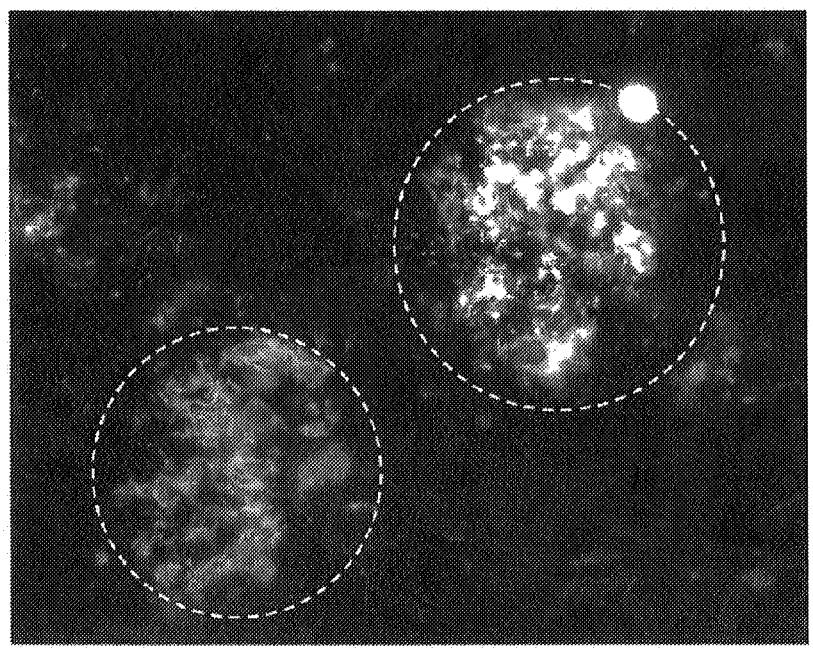

A tetanus toxoid conjugate of the cyclic peptide [Aβ(22-28)-YNGK*], cyclo[EDVGSNKYNGK*] (SEQ ID NO:18) or peptide defined as group 9 in Table 1, elicited antibodies that cross-react in vitro with Aβ (1-42)-oligomers (FIG. 4 or 5) and Aβ (1-42)-fibrils (FIG. 4 or 5). These antibodies also recognize Aβ deposits in post-mortem AD human brain tissue (hippocampus) see FIG. 6. The corresponding conjugate of the linear N-acetylated peptide amide Ac-K*EDVGSNKYNG-NH2 (SEQ ID NO:19) induced good antipeptide antibody titers but the antibodies generated did not recognize oligomeric or fibrillar AP. Thus, the cyclic peptide mimics a conformational epitope in folded Aβ 1-42 that normally does not induce an antibody response. At the time of filing testing of an antibody response to the conjugate with the peptide defined as group 10, the cyclic peptide [Aβ (21-27)-YNGK*] (SEQ ID NO:20) was still in progress.

Materials and Methods

Peptide Synthesis, Purification, and Conjugation

The α-(2,4-dimethoxybenzyl) ester of Na-fluorenylmethoxycarbonyl-L-aspartic acid (Fmoc-Asp-ODmb) was coupled through its side-chain to a polymer for the synthesis of peptide amides (for later conversion of the starting Asp into Asn). The side-chain-protected resin-bound sequence GK*EDVGSNKYD(resin) (SEQ ID NO:21), in which K* is N ε-(S-acetylmercaptoacetyl)lysyl, was then assembled as described earlier (Brugghe et al., 1994). The resin-bound linear peptide was converted to cyclo[GK*EDVGSNKYD (resin)] (SEQ ID NO:21). After side-chain deprotection, except of Lys(SAMA), and cleavage from the resin cyclo [GK*EDVGSNKYN]=cyclo[EDVGSNKYNGK*] (SEQ ID NO:22 triple bonded to SEQ ID NO:18), the peptide from group 9 (Table 1) was obtained. The peptides from groups 4-8 were prepared similarly. The peptide from group 10, cyclo [AEDVGSNYNGK*] SEQ ID NO:20), was prepared from the side-chain-protected resin-bound linear precursor YNGK*AEDVGSD (resin) (SEQ ID NO:23). The peptides were purified by reverse-phase high performance liquid chromatography and characterized by ion-spray mass spectrometry (MH+ found/calculated, see table 1). The purified peptides were coupled to either bromoacetylated tetanus toxoid or maleimidyl-modified bovine serum albumin (BSA) (modifying reagent: NHS-PEO2-Maleimide, Pierce) (Drijfhout J W et al., 2000).

Disaggregation of Aβ(1-42)

Lyophilized Aβ 1-42 (Anaspec) was dissolved in trifluoroacetic acid at a concentration of 1.0 mM, left to stand at room temperature for 1 h and dried under a stream of nitrogen and, thereafter, in a vacuum (1 mm Hg) for 15 min. The peptide was then redissolved in hexafluoroisopropanol at a concentration of 1.0 mM and, after 1 h of incubation at room temperature, dried as described above (Zeng et al., 2001). The peptide was stored at −20° C. for 18-20 h.

Preparation of Oligomeric or Fibrillar Aβ(1-42)

Disaggregated of Aβ 1-42 was dissolved in dimethyl sulfoxide at a concentration of 5.0 mM, diluted 50-fold with either phosphate buffered saline (PBS), pH 7.2, or 10 mM hydrochloric acid. The solution in PBS was incubated at 4° C. for 24 h (to give oligomers), whereas the solution in 10 mM HCl was incubated at 37° C. for 24 h (to give fibrils) (Stine et al).

Immunization of Mice

Groups of eight female Balb/c mice of 6-8 weeks of age were immunized subcutaneously on days 0 and 28 with either 25 μg Aβ 1-42 in PBS without adjuvant or with 50 μg peptide-TTd conjugate and 75 μg AlPO4 in PBS. Small serum samples were collected on day 0. The mice were bled on day 42.

ELISA

Microtitre plates (Greiner 655092) were coated with Aβ 1-42 or peptide-BSA conjugates. Freshly prepared Aβ 1-42 oligomers or fibrils were diluted to a final concentration of 2.5 μM (11.3 μg/ml) in 0.04 M sodium carbonate/bicarbonate buffer, pH 9.7. Peptide-BSA conjugates in phosphate buffered saline, pH 7.2 (PBS), had a total protein concentration of 0.5 μg/ml. Aliquots (100 μl) of these solutions were transferred into wells of the plates. The plates were incubated for 90 min at 37° C. The plates were further processed as described earlier (Westdijk, Van den Ijssel et al., 1997).

Immunohistochemical Staining

Human brain sections of the hippocampus of several donors with Alzheimer disease (Braak 5 or 6) were used (Netherlands Brain Bank). Cryosections (10 μm) were cut from unfixed directly frozen tissue, thaw-mounted, dried for 1 hour and stored in a sealed box at −20 C. For immunostaining, sections were fixed in 4% PFA-PBS solution for 10 min, washed in 0.05 M phosphate buffer (PB) for 10 min with 2 exchanges and blocked with 10% normal donkey serum (NDS)+0.4% TritonX100 in 0.05M PB for 1 hour at RT. The blocking solution was discarded and diluted mouse sera (1:300; first antibody) in 3% NDS+0.4% TritonX100 in 0.05 M PB was added and incubated 0/N at RT in a box with wet tissues. Sections were washed with 0.05M PB; at least 30 min with one or more exchanges. Then sections were incubated with Donkey-anti-Mouse-Cy3 1:1400 in 0.05 M PB for 2 hours. Sections were washed with 0.05M PB; at least 30 min with one or more exchanges. Sections were sealed in Vectashield with Dapi (Vector). Mouse Monoclonal 6E10 to beta amyloid 1-17 (Abcam, Cambridge, UK) was used as positive control (1:15,000).

REFERENCE LIST

Agadjanyan M G, Ghochikyan A, Petrushina IVasilevko V, Movsesyan N, Mkrtichyan M, Saing T, and Cribbs D H, 2005. Prototype Alzheimer's disease vaccine using the immunodominant B cell epitope from β-amyloid and promiscuous T cell epitope pan HLA DR-binding peptide. *J. Immunol.* 174, 1580-1586.

Beuvery, E. C., Roy, R., Kanhai, V., Jennings, H. J., 1986. Characteristics of two types of meningococcal group C polysaccharide conjugates using tetanus toxoid as carrier protein. Dev. Biol. Stand. 65, 197-204.

Blennow K, de Leon M J, and Zetterberg H, 2006. Alzheimer's disease. *Lancet* 368, 387-403.

Brugghe H F, Timmermans H A M, van Unen L M A, ten Hove G J, van de Werken G, Poolman J T, and Hoogerhout P, 1994. Simultaneous multiple synthesis and selective conjugation of cyclized peptides, derived from a surface-loop of a meningococcal class 1 outer membrane protein. *Int. J. Peptide Protein Res.* 43, 166-172.

Check E, 2002. Nerve inflammation halts trial for Alzheimer's drug. *Nature* 415, 462.

Claesson, B. A., Trollfors, B., Lagergard, T., Knutsson, N., Schneerson, R., Robbins, J. B., 2005. Antibodies against Haemophilus influenzae type b capsular polysaccharide and tetanus toxoid before and after a booster dose of the carrier protein nine years after primary vaccination with a protein conjugate vaccine. Pediatr. Infect. Dis. J. 24, 463-464.

Drijfhout J W and Hoogerhout P, 2000. Methods of preparing peptide-carrier conjugates. In: *Fmoc Solid Phase Peptide Synthesis: A Practical Approach* (W. C. Chan and P. D. White, eds.). Oxford University Press, pp. 229-241.

Editorials Nature Med. 2006, Vol. 12, #7 July 2006.

Gelinas D S, DaSilva K, Fenili D, St. George-Hyslop P, and McLaurin J, 2004. Immunotherapy for Alzheimer's disease. *Proc. Natl. Acad. Sci. USA* 101, 14657-14662.

Gevorkian G., Petrushina I, Manoutcharian K, Ghochikyan A, Acero G, Vasilevko V, Cribbs D H, and Agadjanyan M A, 2004. Mimotopes of conformational epitopes in fibrillar β-amyloid. *J. Neuroimmunol.* 156, 10-20.

Ghochikyan A, Mkrtichyan M, Petrushina I, Movsesyan N, Karapetyan A, Cribbs D H, and Agadjanyan M G, 2006. Prototype Alzheimer's disease epitope vaccine induced strong Th2-type anti-Aβ antibody response with Alum to Quil A adjuvant switch. *Vaccine* 24, 2275-2282.

Gilman S, Koller M, Black R S, Jenkins L, Griffith S G, Fox N C, Eisner L, Kirby L, Boada Rovira M, Forette F, and Orgogozo J-M, for the AN1792(QS-21)-201 study team, 2005. Clinical effects of Aβ immunization (AN1792) in patients with AD in an interrupted trial. Neurology 64, 1553-1562.

Haass, C., Selkoe, D. J., 2007. Soluble protein oligomers in neurodegeneration: lessons from the Alzheimer's amyloid beta-peptide. Nat. Rev. Mol. Cell Biol. 8, 101-112.

Henriksen, G., Yousefi, B. H., Drzezga, A., Wester, H. J., 2008. Development and evaluation of compounds for imaging of beta-amyloid plaque by means of positron emission tomography. Eur. J. Nucl. Med. Mol. Imaging 35 Suppl 1, S75-S81.

Hock C, Konietzko U, Papassotiropoulos A, Wollmer A, Streffer J, von Rotz R C, Davey G, Moritz E, and Nitsch R M, 2002. Generation of antibodies specific for beta-amyloid by vaccination of patients with Alzheimer disease. *Nature Med.* 8, 1270-1275.

Hutchinson, E. G., Sessions, R. B., Thornton, J. M., Woolfson, D. N., 1998. Determinants of strand register in antiparallel beta-sheets of proteins. Protein Sci. 7, 2287-2300.

Klein W L, Stine W B, and Teplow D B, 2004. Small assemblies of unmodified amyloid β-protein are the proximate neurotoxin in Alzheimer's disease. *Neurobiol. Aging* 25, 569-580.

Lambert, M. P., Velasco, P. T., Chang, L., Viola, K. L., Fernandez, S., Lacor, P. N., Khuon, D., Gong, Y., Bigio, E. H., Shaw, P., De Felice, F. G., Krafft, G. A., Klein, W. L., 2007. Monoclonal antibodies that target pathological assemblies of Abeta. J. Neurochem. 100, 23-35.

Lee, M., Bard, F., Johnson-Wood, K., Lee, C., Hu, K., Griffith, S. G., Black, R. S., Schenk, D., Seubert, P., 2005. Abeta42 immunization in Alzheimer's disease generates Abeta N-terminal antibodies. Ann. Neurol. 58, 430-435.

Lemere C A, Maier M, Jiang L, Peng Y, and Seabrook T J, 2006. Amyloid-beta immunotherapy for the prevention and treatment of Alzheimer's disease: lessons from mice, monkeys, and humans. *Rejuvenation Res.* 9, 77-84.

Lemere, C. A., Maier, M., Peng, Y., Jiang, L., Seabrook, T. J., 2007. Novel Abeta immunogens: is shorter better? Curr. Alzheimer Res. 4, 427-436.

Maier M, Seabrook T J, Lazo N D, Jiang L, Das P, Janus C, and Lemere C A, 2006. Short amyloid β (Aβ) immunogens reduce cerebral Aβ load and learning deficits in an Alzheimer's disease mouse model in the absence of an Aβ-specific cellular immune response. *J. Neurosci.* 26, 4717-4728.

McDonnell J, Redekop W K, Van der Roer N, Goes E, Ruitenberg A, Busschbach J J, Breteler M M, and Rutten F F, 2001. The cost of treatment of Alzheimer's disease in The Netherlands: a regression-based simulation model. *Pharmacoeconomics* 19, 379-390.

McLaurin J, Cecal R, Kierstead M E, Tian X, Phinney A L, Manea M, French J E, Lambermon M H L, Darabie A A, Brown M E, Janus C, Chishti M A, Horne P, Westaway D, Fraser P E, Mount H T J, Przybylski M, and St George-Hyslop P, 2002. Therapeutically effective antibodies against amyloid-beta peptide target amyloid-beta residues 4-10 and inhibit cytotoxicity and fibrillogenesis. *Nature Med.* 1263-1269.

Meyer-Luehmann, M., Spires-Jones, T. L., Prada, C., Garcia-Alloza, M., de, C. A., Rozkalne, A., Koenigsknecht-Talboo, J., Holtzman, D. M., Bacskai, B. J., Hyman, B. T., 2008. Rapid appearance and local toxicity of amyloid-beta plaques in a mouse model of Alzheimer's disease. Nature 451, 720-724.

Movsesyan, N., Ghochikyan, A., Mkrtichyan, M., Petrushina, I., Davtyan, H., Olkhanud, P. B., Head, E., Biragyn, A., Cribbs, D. H., Agadjanyan, M. G., 2008. Reducing AD-like pathology in 3xTg-AD mouse model by DNA epitope vaccine—a novel immunotherapeutic strategy. PLoS. ONE. 3, e2124.

O'Brien, J. T., 2007. Role of imaging techniques in the diagnosis of dementia. Br. J. Radiol. 80 Spec No 2, S71-S77.

Olofsson A, Sauer-Eriksson A E, and Ohman A, 2006. The solvent protection of Alzheimer amyloid-β-(1-42) fibrils as determined by solution NMR spectroscopy. *J. Biol. Chem.* 281, 477-483.

Oomen, C. J., Hoogerhout, P., Bonvin, A. M., Kuipers, B., Brugghe, H., Timmermans, H., Haseley, S. R., van, A. L., Gros, P., 2003. Immunogenicity of peptide-vaccine candidates predicted by molecular dynamics simulations. J. Mol. Biol. 328, 1083-1089.

Oomen C J, Hoogerhout P, Kuipers B, Vidarsson G, van Alphen L, and Gros P, 2005. Crystal structure of an anti-meningococcal subtype P1.4 PorA antibody provides basis for peptide-vaccine design. *J. Mol. Biol.* 351, 1070-1080.

Sadowski M and Wisniewski T, 2004. Vaccines for conformational disorders. Expert Rev. Vaccines 3, 279-290.

Sawaya M R, Sambashivan S, Nelson R, Ivanova M I, Sievers S A, Apostol M, Thompson M J, Balbirnie M, Wiltzius J J W, McFarlane H T, Madsen A Ø, Riekel C, and Eisenberg D, 2007. Atomic structures of amyloid cross-beta spines reveal varied steric zippers. *Nature* 447, 453-457.

Schenk, Barbour R, Dunn W, Gordon G, Grajeda H, Guido T, Hu K, Huang J, Johnson-Wood K, Khan K, Kholodenko D, Lee M, Liao Z, Lieberburg I, Motter R, Mutter L, Soriano F, Shopp G, Vasquez N, Vandevert C, Walker S, Wogulis M, Yednock T, Games D, and Seubert P, 1999. Immunization with amyloid-beta attenuates Alzheimer-disease-like pathology in the PDAPP mouse. *Nature* 400, 173-177.

Sigurdsson E M, Knudsen E, Asuni A, Fitzer-Attas C, sage D, Quartermain D, Goni F, Frangione B, and Wisniewski T, 2004. An attenuated immune response is sufficient to enhance cognition in an Alzheimer's disease mouse model immunized with amyloid-β derivatives. *J. Neurosci.* 24, 6277-6282.

Stine W B, Jr, Dahlgren K N, Krafft G A, LaDu M J, 2003. *J. Biol. Chem.,* 278:11612. Tomiyama, T., Nagata, T., Shimada, H., Teraoka, R., Fukushima, A., Kanemitsu, H., Takuma, H., Kuwano, R., Imagawa, M., Ataka, S., Wada, Y., Yoshioka, E., Nishizaki, T., Watanabe, Y., Mori, H., 2008. A new amyloid beta variant favoring oligomerization in Alzheimer's-type dementia. Ann. Neurol. 63, 377-387.

Vas C J, Rajkumar S, Tanyakitpisal P, and Chandra V, 2001. Alzheimer's disease: the brain killer. *Report of the World Health Organization*.

Walsh, D. M., Selkoe, D. J., 2007. A beta oligomers—a decade of discovery. J. Neurochem. 101, 1172-1184.

Westdijk, J., Van den Ijssel, J., Thalen, M., Beuvery, C., Jiskoot, W., 1997. Quantification of cell-associated and free antigens in Bordetella pertussis suspensions by antigen binding ELISA. J. Immunoassay 18, 267-284.

Woolfson, D. N., Evans, P. A., Hutchinson, E. G., Thornton, J. M., 1993. Topological and stereochemical restrictions in beta-sandwich protein structures. Protein Eng 6, 461-470.

Zeng H, Zhang Y, Peng L-J, Shao H, Menon N K, Yang J, Salomon A R, Freidland R P, and Zagorski M G, 2001. Nicotine and amyloid formation. *Biol. Psychiatry* 49, 248-257.

---

The invention claimed is:

1. A cyclic peptide composition, the formula of which is (a) $X_2X_3$VGSNK-Z (SEQ ID NO:2) or (b) $X_3$VGSNKG-Z (SEQ ID NO:3), wherein:

$X_2$ is E, G, Q or K, $X_3$ is D or N, and

Z is a tetrapeptide fragment that stabilizes a bend present in the cyclic peptide $X_2X_3$VGSNK (SEQ ID NO:2) or $X_3$VGSNKG (SEQ ID NO:3) and is linkable to an immunogenic carrier molecule, wherein Z is selected from the group consisting of YNGK (SEQ ID NO:5),
TCGV (SEQ ID NO:6),
CGNT (SEQ ID NO:7),
LCGT (SEQ ID NO:8),
LKGT (SEQ ID NO:9),
TcGV (SEQ ID NO:14),
LcGT (SEQ ID NO:16) and
LkGT (SEQ ID NO:17), wherein amino acid residue c is D-cysteine and amino acid residue k is D-lysine.

2. An immunogenic composition comprising the cyclic peptide composition according to claim 1 conjugated to said immunogenic carrier molecule.

3. The immunogenic composition according to claim 2, wherein the conjugation is through a selective covalent linkage of Z to the carrier molecule.

4. The immunogenic composition according to claim 2, wherein the carrier molecule is tetanus toxoid.

5. A method for producing the immunogenic composition of claim 2, comprising:

(a) synthesizing the cyclic peptide composition; and (b) conjugating the cyclic peptide composition obtained in step (a) to an immunogenic carrier molecule.

6. The immunogenic composition of claim 3, wherein the selective covalent linkage of the tetrapeptide Z to said immunogenic carrier molecule links a sulfur atom on Z to a sulfhydryl-reactive group of the carrier molecule.

7. The immunogenic composition of claim 6 wherein the sulfur atom of Z is either (a) the sulfhydryl group of the C or c residue of Z, or (b) an S-acetylmercaptoacetyl group modifying the K or k residue of Z.

8. The immunogenic composition according to claim 6, wherein the carrier molecule is tetanus toxoid.

9. A method for producing the immunogenic composition of claim 3, comprising:

(a) synthesizing the cyclic peptide composition, and (b) conjugating the cyclic peptide composition obtained in step (a) to an immunogenic carrier molecule.

10. A method for producing the immunogenic composition of claim 4, comprising:

(a) synthesizing the cyclic peptide composition, and (b) conjugating the cyclic peptide composition obtained in step (a) to the tetanus toxoid molecule.

11. A method for producing the immunogenic composition of claim 6, comprising:

(a) synthesizing the cyclic peptide composition, and (b) conjugating the cyclic peptide composition obtained in step (a) to an immunogenic carrier molecule.

12. A method for producing an immunogenic composition of claim 7, (a) synthesizing the cyclic peptide composition, and (b) conjugating the cyclic peptide composition obtained in step (a) to an immunogenic carrier molecule.

13. A method for producing an immunogenic composition of claim 8, (a) synthesizing the cyclic peptide composition, and (b) conjugating the cyclic peptide composition obtained in step (a) to the tetanus toxoid molecule.

* * * * *

SEQUENCE LISTING

```
<160> NUMBER OF SEQ ID NOS: 23

<210> SEQ ID NO 1
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala or Gly
<220> FEATURE:
<221> NAME/KEY: MISC_FEATURE
<222> LOCATION: (2)..(2)
<223> OTHER INFORMATION: Xaa = Glu, Gly, Gln or Lys
<220> FEATURE:
<221> NAME/KEY: MISC_FEATURE
<222> LOCATION: (3)..(3)
<223> OTHER INFORMATION: Xaa = Asp or Asn

<400> SEQUENCE: 1

Xaa Xaa Xaa Val Gly Ser Asn
1               5

<210> SEQ ID NO 2
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Glu, Gly, Gln or Lys
<220> FEATURE:
<221> NAME/KEY: MISC_FEATURE
<222> LOCATION: (2)..(2)
<223> OTHER INFORMATION: Xaa = Asp or Asn
```

```
<400> SEQUENCE: 2

Xaa Xaa Val Gly Ser Asn Lys
1               5

<210> SEQ ID NO 3
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Asp or Asn

<400> SEQUENCE: 3

Xaa Val Gly Ser Asn Lys Gly
1               5

<210> SEQ ID NO 4
<211> LENGTH: 42
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 5
<211> LENGTH: 4
<212> TYPE: PRT
<213> ORGANISM: Artificial
<220> FEATURE:
<223> OTHER INFORMATION: Synthetic

<400> SEQUENCE: 5

Tyr Asn Gly Lys
1

<210> SEQ ID NO 6
<211> LENGTH: 4
<212> TYPE: PRT
<213> ORGANISM: Artificial
<220> FEATURE:
<223> OTHER INFORMATION: Synthetic

<400> SEQUENCE: 6

Thr Cys Gly Val
1

<210> SEQ ID NO 7
<211> LENGTH: 4
<212> TYPE: PRT
<213> ORGANISM: Artificial
<220> FEATURE:
<223> OTHER INFORMATION: Synthetic

<400> SEQUENCE: 7

Cys Gly Asn Thr
1
```

```
<210> SEQ ID NO 8
<211> LENGTH: 4
<212> TYPE: PRT
<213> ORGANISM: Artificial
<220> FEATURE:
<223> OTHER INFORMATION: Synthetic

<400> SEQUENCE: 8

Leu Cys Gly Thr
1

<210> SEQ ID NO 9
<211> LENGTH: 4
<212> TYPE: PRT
<213> ORGANISM: Artificial
<220> FEATURE:
<223> OTHER INFORMATION: Synthetic

<400> SEQUENCE: 9

Leu Lys Gly Thr
1

<210> SEQ ID NO 10
<211> LENGTH: 4
<212> TYPE: PRT
<213> ORGANISM: Artificial
<220> FEATURE:
<223> OTHER INFORMATION: Synthetic

<400> SEQUENCE: 10

Gly Ala Ile Lys
1

<210> SEQ ID NO 11
<211> LENGTH: 4
<212> TYPE: PRT
<213> ORGANISM: Artificial
<220> FEATURE:
<223> OTHER INFORMATION: Synthetic

<400> SEQUENCE: 11

Gly Ala Ile Cys
1

<210> SEQ ID NO 12
<211> LENGTH: 4
<212> TYPE: PRT
<213> ORGANISM: Artificial
<220> FEATURE:
<223> OTHER INFORMATION: Synthetic

<400> SEQUENCE: 12

Ala Ile Ile Lys
1

<210> SEQ ID NO 13
<211> LENGTH: 4
<212> TYPE: PRT
<213> ORGANISM: Artificial
<220> FEATURE:
<223> OTHER INFORMATION: Synthetic

<400> SEQUENCE: 13

Ala Ile Ile Cys
1

<210> SEQ ID NO 14
```

```
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Cys

<400> SEQUENCE: 14

Thr Xaa Gly Val
1

<210> SEQ ID NO 15
<211> LENGTH: 4
<212> TYPE: PRT
<213> ORGANISM: Artificial
<220> FEATURE:
<223> OTHER INFORMATION: Synthetic

<400> SEQUENCE: 15

Cys Gly Asn Thr
1

<210> SEQ ID NO 16
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Cys

<400> SEQUENCE: 16

Leu Xaa Gly Thr
1

<210> SEQ ID NO 17
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Lys

<400> SEQUENCE: 17

Leu Xaa Gly Thr
1

<210> SEQ ID NO 18
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Lys is substituted at epsilon-nitrogen by
      S-acetylmercaptoacetyl

<400> SEQUENCE: 18

Glu Asp Val Gly Ser Asn Lys Tyr Asn Gly Lys
1               5                   10
```

```
<210> SEQ ID NO 19
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Lys is substituted at epsilon-nitrogen by
      S-acetylmercaptoacetyl

<400> SEQUENCE: 19

Lys Glu Asp Val Gly Ser Asn Lys Tyr Asn Gly
1               5                   10

<210> SEQ ID NO 20
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Lys is substituted at epsilon-nitrogen by
      S-acetylmercaptoacetyl

<400> SEQUENCE: 20

Ala Glu Asp Val Gly Ser Asn Tyr Asn Gly Lys
1               5                   10

<210> SEQ ID NO 21
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Lys is substituted at epsilon-nitrogen by
      S-acetylmercaptoacetyl

<400> SEQUENCE: 21

Gly Lys Glu Asp Val Gly Ser Asn Lys Tyr Asp
1               5                   10

<210> SEQ ID NO 22
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Lys is substituted at epsilon-nitrogen by
      S-acetylmercaptoacetyl

<400> SEQUENCE: 22

Gly Lys Glu Asp Val Gly Ser Asn Lys Tyr Asn
1               5                   10

<210> SEQ ID NO 23
<211> LENGTH: 11
<212> TYPE: PRT
<213> ORGANISM: Artificial
<220> FEATURE:
```

-continued

```
<223> OTHER INFORMATION: Synthetic
<220> FEATURE:
<221> NAME/KEY: MOD_RES
<222> LOCATION: (4)..(4)
<223> OTHER INFORMATION: Lys is substituted at epsilon-nitrogen by
      S-acetylmercaptoacetyl

<400> SEQUENCE: 23

Tyr Asn Gly Lys Ala Glu Asp Val Gly Ser Asp
1               5                   10
```